United States Patent [19]

Bauer

[11] Patent Number: 4,646,340
[45] Date of Patent: Feb. 24, 1987

[54] SCATTER RADIATION GRID DRIVE

[75] Inventor: Manfred Bauer, Brunsbek, Fed. Rep. of Germany

[73] Assignee: U.S. Philips Corporation, New York, N.Y.

[21] Appl. No.: 605,532

[22] Filed: Apr. 30, 1984

[30] Foreign Application Priority Data

May 3, 1983 [DE] Fed. Rep. of Germany ....... 3316003

[51] Int. Cl.$^4$ ................... G21K 1/04; G03B 41/16
[52] U.S. Cl. ..................................... 378/155; 378/154
[58] Field of Search ................ 378/154, 155, 140, 149

[56] References Cited

U.S. PATENT DOCUMENTS

| 2,132,774 | 10/1938 | Brown | 378/155 |
| 2,208,265 | 7/1940 | Kizaur | 378/155 |
| 2,767,323 | 10/1956 | Stava et al. | 378/155 |

FOREIGN PATENT DOCUMENTS 2733613  2/1979  Fed. Rep. of Germany ...... 378/155

Primary Examiner—Craig E. Church
Assistant Examiner—Charles Wieland
Attorney, Agent, or Firm—Marc D. Schechter

[57] ABSTRACT

The invention relates to a scatter grid drive for oscillating a scatter grid back and forth during an exposure. The reversal point, at which the direction of movement of grid is reversed, is passed so quickly that there is little risk of imaging the grid in the radiograph.

2 Claims, 5 Drawing Figures

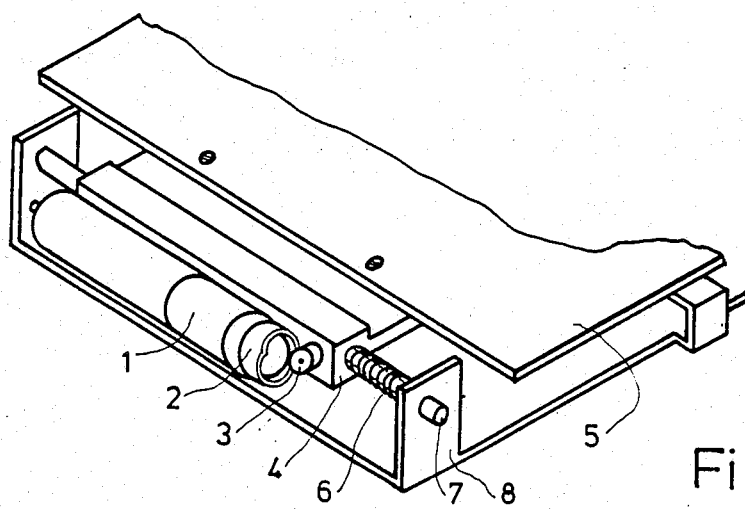
Fig. 1
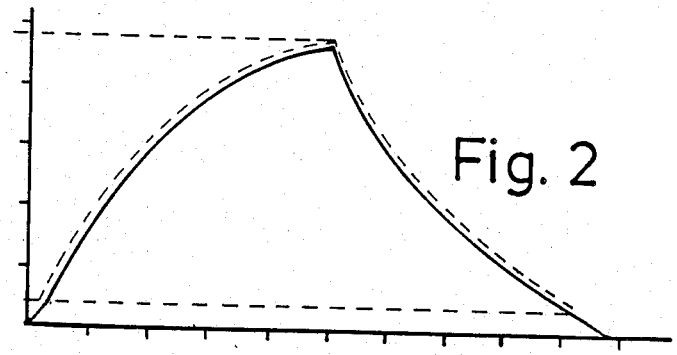
Fig. 2
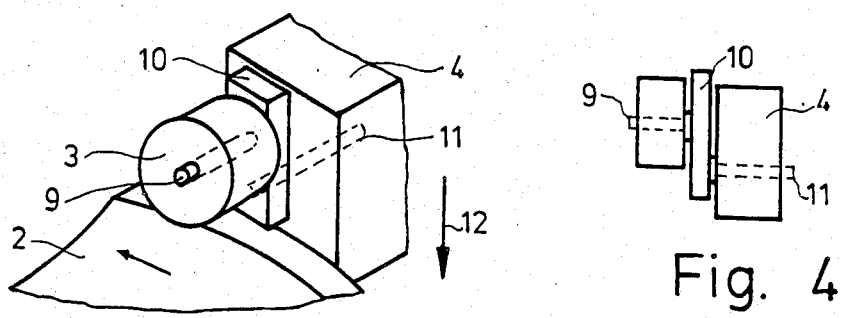
Fig. 3
Fig. 4
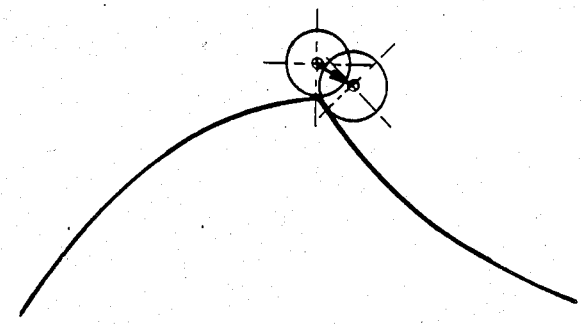
Fig. 5

SCATTER RADIATION GRID DRIVE

BACKGROUND OF THE INVENTION

The invention relates to a device for an X-ray apparatus, for removing scattered radiation. Scattered radiation is removed a scatter grid which is coupled to a roller. The roller is pressed against a cam. The surface of the cam is shaped so that during a rotation of the cam, the point of contact with the roller is shifted in a direction perpendicular to the cam's shaft.

A device as described above is described in German Offenlegungsschrift No. 2,733,613. In this device, rotation of the cam causes the scatter grid to be displaced perpendicularly to the direction of its laminations in order to prevent imaging of the grid during an X-ray exposure.

The scatter grid must be displaced comparatively quickly at the beginning of each exposure because the exposure duration cannot be predicted when an automatic exposure device is used, and because imaging of the grid must be avoided even for short exposures. Since the maximum displacement of the grid (the so-called stroke) is usually limited for structural reasons in devices of this kind, the scatter grid is oscillated back and forth in many known devices in order to remove the scattered radiation. However, there is a risk that the grid laminations will be imaged when the grid reverses direction because the scatter grid becomes momentarily stationary at these reversals several times during an exposure.

In the device described in German Offenlegungsschrift No. 2,733,613 the risk of imaging the grid is eliminated by journalling the roller eccentrically on the scatter grid (or on a part which is connected thereto) so that the position where the grid reverses direction changes. However, this device requires a comparatively fast drive, so that the grid reverses direction several times during an exposure. Consequently, the X-ray apparatus may start to oscillate, thus affecting the sharpness of the X-ray image.

SUMMARY OF THE INVENTION

It is an object of the invention to provide a device for removing scattered radiation in which the grid reverses direction so quickly that there is little risk of imaging the grid.

This object is achieved by connecting the roller to a lever so that the roller is rotatable about its center. The lever is connected to the scatter grid, directly or indirectly, so as to be pivotable about a pivot shaft which is parallel to the shaft of the roller. The distance between the pivot shaft and the roller shaft is equal to or only slightly larger than the radius of the roller. The surface of the cam is shaped so that at the reversal point at which the roller has reached its maximum displacement against the force, the slope of the cam surface is discontinuous.

The operation of the invention cam be explained as follows. The surface of the cam which cooperates with the roller is shaped so that the slope at the reversal point is discontinuous. If the scatter grid could directly follow the contour of the cam, the desired oscillation of the grid could be obtained with a short standstill at each reversal. However, because the roller has a finite diameter, the center of the roller follows a rounded path as it rolls on the surface of the cam. If the scatter grid were to follow this rounded path, a comparatively long standstill would occur at each reversal.

However, this is avoided according to the invention by connecting the scatter grid not to the roller shaft, but rather to the pivot shaft of a lever on which the roller is journalled. Because the scatter grid is pressed, for example by a spring, against the cam via the roller which is coupled to the lever, the connecting line between the roller shaft and the pivot shaft is always perpendicular to the surface of the cam. When the slope of the cam surface changes discontinuously at the reversal point, the angular position of the connecting line between the pivot shaft and the roller shaft, and hence the position of the pivot shaft which defines the position of the scatter grid, abruptly change when the roller passes the reversal point. Consequently, the pivot shaft, and hence the scatter grid, can more quickly follow the contour of the cam, even though the roller shaft cannot do so because of the finite diameter of the roller.

BACKGROUND OF THE INVENTION

FIG. 1 is a a perspective view of the scatter grid drive according to the invention.

FIG. 2 is a graph of a portion of the surface of the cam.

FIG. 3 is a perspective view of a detail of the drive according to the invention.

FIG. 4 is a side elevational view of a portion of the drive shown in FIG. 3.

FIG. 5 schematically illustrates the behavior of the roller at the area of the reversal point.

DESCRIPTION OF THE PREFERRED EMBODIMENTS

In FIG. 1, the scatter grid drive includes a drive motor 1 which rotates a cam 2 having an annular cross-section at a constant angular speed. The end face of the cam 2 is in contact with a roller 3. Roller 3 has a roller shaft which extends perpendicular to the shaft of the cam 2. The roller is coupled to a shoe 4 which is rigidly connected to the scatter grid 5. The laminations (not shown) of grid 5 extend perpendicular to the shaft of the cam 2.

The shoe 4 to which the roller 3 is coupled is guided on a guide rod 7 which extends parallel to the shaft of the cam 2. A spring 6 is provided on guide rod 7 to press shoe 4 so that the roller 3, which is coupled thereto, is pressed against the end face of the cam 2. The components are mounted and secured on a support 8.

The unit shown in FIG. 1 is particularly suitable for mammography.

FIG. 2 shows a development of a portion of the end face of the cam 2 in the form of a graph of the height of the end face of the cam (measured in the direction of the shaft of the cam) as a function of the angle of rotation. The rotary movement of cam 2 always commences with the shoe 4 in its closest position of the motor 1 (i.e. at the lowest reversal point).

As shown in FIG. 2, the curve initially rises comparatively steeply. Then, the curve becomes flatter. The initial steep rise of the curve ensures that for short exposures, where the cam rotates through only part of the curve during the exposure, the scatter grid is moved so quickly that its laminations are not imaged in the radiograph.

The increasingly flatter curve ultimately reaches a maximum value at in the upper reversal point. At the upper reversal point the roller 3 has been shifted furthest against the spring force. The curve subsequently falls abruptly with initially a large steepness and gradually a decreasing steepness, until the starting position is reached again. Due to this geometry of the end face of the cam 2, the end face has a discontinuous slope at the area of maximum displacement.

As shown in FIG. 3, the roller 3 is not directly connected to the shoe 4. Instead the roller shaft 9 is supported by a lever 10. Lever 10 is journalled on the shoe 4 so as to be pivotable about the shaft 11. Shaft 11 is parallel to the roller shaft 9.

As shown in FIG. 4, the distance between the roller shaft 9 and the pivot shaft 11 corresponds exactly to the radius of the roller 3. Because, moreover, the spring force (symbolized by vector 12) acts on the shoe 4, the lever 10 always occupies a position such that an imaginary connecting line between the two shafts extends perpendicular to the surface of the cam 2. Consequently, the pivot shaft 11 (and hence also the shoe 4 and the scatter grid 5) follows the contour of the end face of the cam 2.

Shaft 11 follows the contour of the end face of cam 2 even when the roller 3 reaches and passes the peak (and the scatter grid 5 reaches and passes the reversal point). However, because the rise in the surface of the cam 2 then changes abruptly, the position of the roller shaft 9 also changes abruptly, as shown in FIG. 5. Subsequently, the roller shaft moves downward, like the pivot shaft 11, according to the variation of the curve of the end face of cam 2 and reaches the lower reversal point. Because the upper reversal point is abruptly passed by the roller 3, imaging of the grid 5 is substantially precluded.

The device according to the invention thus oscillates the scatter grid 5 back and forth sufficiently fast to adequately erase an image of the grid with a stroke (the distance between the upper and the lower reversal points) of just 10 mm and a 5 second rotation of the cam.

FIG. 1 shows the cam 2 as a hollow cylindrical body. However, it is in principle also possible to utilize a disc instead. The disc would then be rotated about a shaft which is parallel to the shaft of the roller 3, and would have a discontinuous slope at its point which is situated furthest from its shaft (and which determines the upper reversal point of the grid). This construction, however, is generally less compact than that shown in FIG. 1, because the motor must then be mounted rotated through 90° as compared to the orientation shown in FIG. 1.

What is claimed is:

1. A device for reducing scattered radiation comprising:
    a scatter grid;
    a lever arm having first and second opposite ends, the first end being pivotably connected to the scatter grid;
    a roller rotatably connected to the second end of the lever arm;
    a cam having a surface; and
    means for pressing the roller against the cam surface by applying a force to the first end of the lever arm;
    characterized in that:
    the roller has a radius, and the lever has a length between the first and second ends which is equal to or only slightly larger than the radius of the roller; and
    the cam surface has a slope which changes discontinuously at a point where the roller has a maximum displacement against the pressing means.

2. A device as claimed in claim 1, characterized in that the cam is a hollow cylinder.

* * * * *